US00PP09769P

United States Patent [19]

Maltagliati

[11] Patent Number: Plant 9,769

[45] Date of Patent: Dec. 31, 1996

[54] HYBRID TEA ROSE PLANT NAMED 'MALJOANNA'

[76] Inventor: Mark G. Maltagliati, 1698 Manor Dr., San Pablo, Calif. 94801

[21] Appl. No.: 582,351

[22] Filed: Jan. 19, 1996

[51] Int. Cl.[6] ..... A01H 5/00

[52] U.S. Cl. ..... Plt./18

[58] Field of Search ..... Plt./18, 19

*Primary Examiner*—Howard J. Locker

[57] ABSTRACT

A new and distinct Hybrid Tea rose variety distinguished by forming attractive pink blossoms on very straight stems with large semi glossy foliage. The new variety is long lasting and can be grown to advantage for the production of cut flowers.

1 Drawing Sheet

The present invention applies to a new and distinctive variety of rose plant of the Hybrid Tea class, originating by my crossing "Silver Anniversary" variety U.S. Plant Pat. No. 7,658 as the seed parent, (the "Silver Anniversary" variety is sometimes referred to as "Heather" or JACLAV variety), with an unknown light pink Hybrid Tea class rose as the pollen parent.

The new variety Hybrid Tea rose plant possesses many splendid characteristics including:

(a) A very erect growth habit with few thorns.
(b) Forms fully double medium pink flowers which usually set one per stem.
(c) Flowers are long lasting on or off the plant.
(d) Forms elegant foliage and placement.
(e) Exhibits good disease resistance.

The new variety is appropriate for the needs of the floriculture industry. It can be grown to produce attractive cut flowers in greenhouses or outdoors.

Asexual reproduction of the new variety is executed by a number of routes, including splice grafting onto an understock of *Rosa odorata,* performed at Richmond, Calif. shows that the aforementioned and all other distinctive characteristics are strictly transmissible from one generation to another.

The new variety has been named the MALJOANNA variety.

The accompanying drawing shows typical specimens of the vegetative growth and flowers of the new variety in different stages of development and as depicted in color as nearly true as it is reasonably possible to make the same in a color illustration of this character. Center, top, and proceeding clockwise; a fully open flower and stem, flowering bud about four weeks old, flower bud after sepals divide, a three leaflet leaf (reverse view), five leaflet leaf (obverse view), a flower bud in the course of opening, a typical young shoot.

The following is a detailed description of my new variety, with color terminology in accordance with the Royal Horticultural Society Colour Chart (RHSCC). The terminology used in the color description herein refers to plate numbers in the aforementioned color chart, e.g. "53A" is plate "53A" of the Royal Horticultural Society Colour Chart.

Parentage:

*Seed parent.*—Silver Anniversary™ (JACLAV), U.S. Plant Pat. No. 7,658.

*Pollen parent.*—An unknown light pink in the Hybrid Tea class.

Class: Hybrid Tea.

The following observations are made of specimens grown indoors in Contra Costa county, Calif., year round.

FLOWER

Blooming habit

A. Bud:
(1) *Size.*—Fully mature, sepals enclosed, 3–3.5 cm from base of sepals.
(2) *Form.*—Pointed.
(3) *Sepals.*—3–3.5 cm/in length; with irregular extensions of 1 to 3 cm in length: sepal edge serration with appendages is irregular. Usually one and sometimes three sepals show appendages of 0.5 to 1.5 cm in width. Light cotton matting on inner surface of sepals, smooth on outer surface. Inside color — 147C; outside 146A.
(4) *Peduncle.*—Length — 12 to 16 cm: Surface — smooth, no prickles, no hairs. Strength— stiff, heavy. Color — 146A.
(5) *Receptacle.*—Shape. — attenuate, gradually tapering, round. Color — 146A.
(6) *Color.*—When sepals first divide, near to 51B.

B. Bloom:
(1) *Size.*—When open — 10 to 11 cm.
(2) *Borne.*—Singly.
(3) *Form.*—Fully double, symmetrical, regular.
(4) *Petalage.*—Between — 36 to 40.
(5) *Color.*—Early open 56C inside; 56B outside. Fully open close to 56D inside; 55C outside.

C. Petals:
(1) *Texture.*—Turgid.
(2) *Appearance.*—Slightly shiney, smooth upper surface: lower surface dull, smooth.
(3) *Form.*—Rounded; base to top edge: 6 cm; horizontal; center: 5 cm.
(4) *Arrangement.*—Layered, evenly distributed.
(5) *Petaloids in center.*—Three to four, irregular.
(6) *Persistence.*—Long lasting, drop off cleanly.
(7) *Fragrance.*—Light, spicy.
(8) *Lasting quality.*—10 to 12 days when cut or left on plant.

REPRODUCTIVE ORGANS

A. Stamen:
(1) *Arrangement.*—Regularly arranged around styles.
(2) *Number.*—Average — 60 to 65.
(3) *Length.*—Average — 6 to 10 mm.
(4) *Filaments.*—Color — close to 51A.
(5) *Anthers.*—Color — 12D.

(6) *Pollen.*—Color — close to 14B.

B. Pistil:

(1) *Styles.*—Length. — 6 to 8 mm exposed; number 55 to 60, with many fine white hairs at base; color: near to 54B.

(2) *Stigma.*—Color. — between 16B&C.

(3) *Ovary.*—Shape — orbicular, poorly developed, narrow, exposed from receptacle; average diameter 1.5 cm; average height 0.5 cm.

C. Hips: None observed.

PLANT

A. Form: Upright.

B. Growth: Vigorous.

*Height.*—Average 2.5 m.

C. Stem length.

*Basal break to flower bud tip.*—Average — 85 cm.

D. Foliage: Compound of 3 to 5 leaflets on bloom stem.

(1) *Mature size.*—5 leaflet leaf—15 to 20 cm, measured from base of stipule to terminal leaflet tip.

(2) *Quantity.*—Stems average 12 to 14 nodes.

(3) *Color.*—New foliage upper side close to 146AB with overtones of 184AB; under side 184B. Mature foliage upper side 147A; under side 138A.

(4) *Shape.*—Ovate, serrate, acute.

(5) *Texture.*—Thick, waxy, semiglossy.

(6) *Edge.*—Serrated in various degrees, with base of leaflet almost entire to strongly serrate at apex.

(7) *Rachis.*—A few fine glandular hairs on upper side at margin. Four to five prickles on under side, 0.5 to 2 mm long.

(8) *Stipules.*—Very fine glandular serration on edge. Auricles face forward, parallel form. Length of stipule from petal base to tip of auricle 2 to 2.5 cm, width 5 to 8 mm.

E. Resistance to disease: Good.

F. Wood:

*New wood.*—Color 146B.

*Old wood.*—Color 146A.

G. Thorns: Needle shaped, curving slightly downward, 1 to 1.5 cm long; spaced irregularly on lower third of stems. Average 10 per stem.

*Color.*—152D older; 167B younger.

H. Winter hardiness: Good.

I claim:

1. A new and distinct variety of rose plant of the Hybrid Tea class, substantially as herein shown and described.

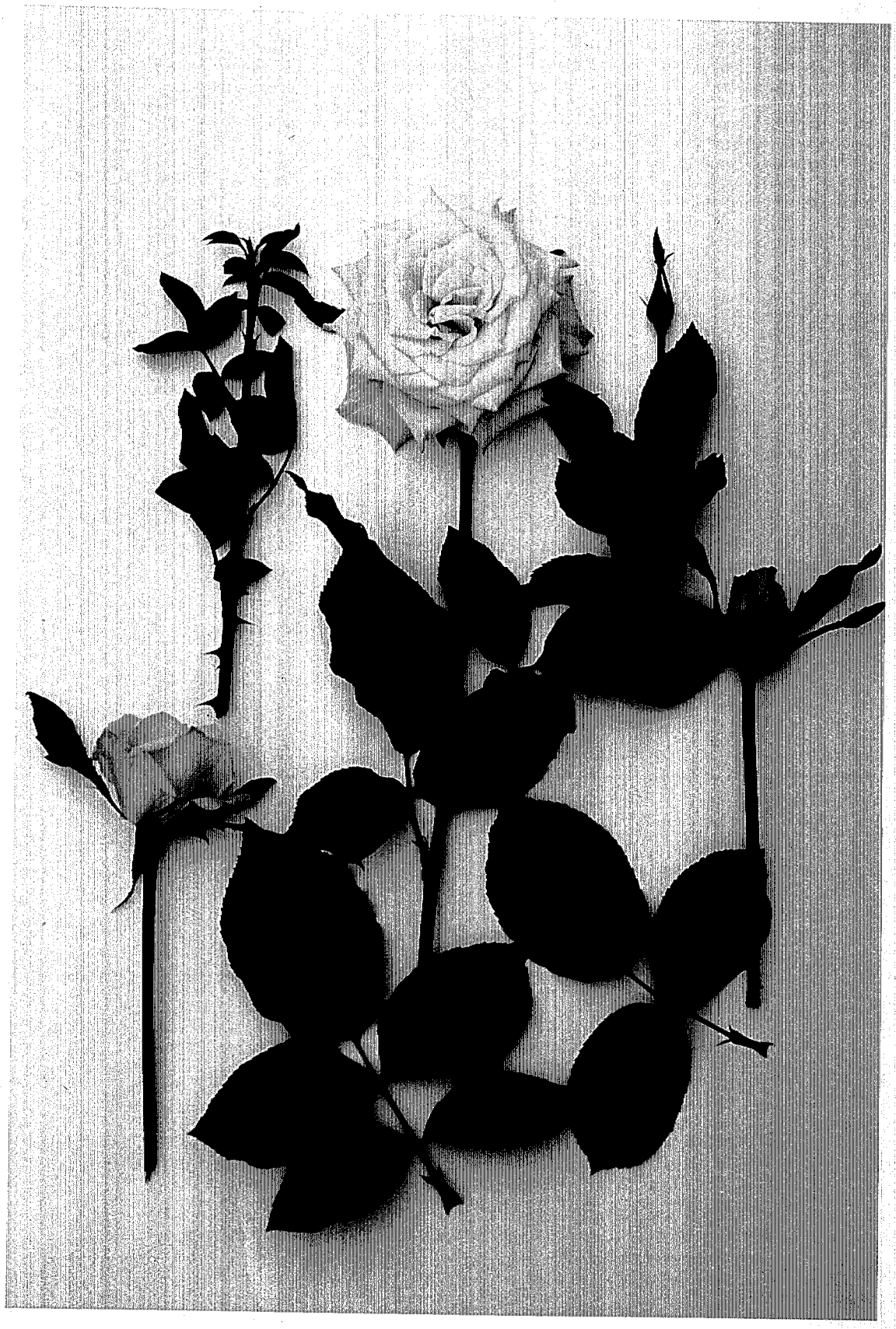

* * * * *